United States Patent [19]

Nakashima et al.

[11] Patent Number: 4,931,440
[45] Date of Patent: Jun. 5, 1990

[54] URICOSURIC COMPOSITION

[75] Inventors: Mitsuyoshi Nakashima, Hamamatsu; Mitsutaka Kanamaru, Nagoya; Akira Sugiyama, Ikoma; Masato Terakawa, Nara, all of Japan

[73] Assignee: Fujisawa Pharmaceutical Company, Ltd., Osaka, Japan

[21] Appl. No.: 221,654

[22] Filed: Jul. 20, 1988

[30] Foreign Application Priority Data

Jul. 29, 1987 [JP] Japan .................. 62-189822

[51] Int. Cl.$^5$ ........................................ A61K 31/505
[52] U.S. Cl. ................... 514/259; 514/825; 514/891
[58] Field of Search ........................ 514/259, 825, 891

[56] References Cited

U.S. PATENT DOCUMENTS 4,734,419  3/1988  Hashimoto et al. .............. 514/259

Primary Examiner—Douglas W. Robinson
Assistant Examiner—Raymond J. Henley, III
Attorney, Agent, or Firm—Oblon, Spivak, McClelland, Maier & Neustadt

[57] ABSTRACT

The invention relates to a method for preventing and/or treating gout and hyperuricemia which comprises administering a uricosuric effective amount of a quinazoline derivative of the general formula:

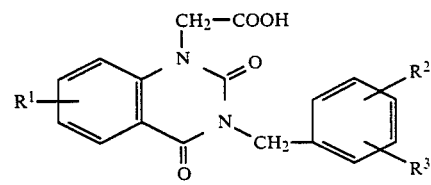

wherein $R^1$, $R^2$ and $R^3$ each is a hydrogen atom or a halogen atom or a pharmaceutically acceptable salt thereof to a human being in need thereof.

3 Claims, No Drawings

URICOSURIC COMPOSITION

INDUSTRIAL FIELD OF UTILIZATION

This invention relates to a uricosuric composition comprising a quinazoline derivative of the following general formula (I) or a pharmaceutically acceptable salt thereof as an active ingredient, and, as such, finds application in the field of health care.

1. Prior Art

The quinazoline derivative (I) according to this invention is a known compound and has been demonstrated to have aldose reductase-inhibitory activity [Japanese Unexamined Pat. application No. KOKAI 62-96476 (1987)]. It is not known, however, that the derivative has uricosuric activity.

2. Construction of the Invention

This invention relates to a uricosuric composition comprising a quinazoline derivative of the general formula (I):

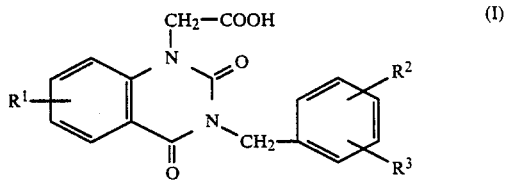

wherein $R^1$, $R^2$ and $R^3$ each is a hydrogen atom or a halogen atom or a pharmaceutically acceptable salt thereof as an active ingredient.

In the above definition of quinazoline derivative (I), the halogen designated independently by $R^1$, $R^2$ and $R^3$ includes chlorine, bromine, iodine and fluorine.

The pharmaceutically acceptable salt of quinazoline derivative (I) includes salts with inorganic bases such as alkali metals (e.g. sodium, potassium, etc.) and alkaline earth metals (e.g. calcium, magnesium, etc.), ammonium salts, salts with organic bases such as organic amines (e.g. triethylamine, pyridine, picoline, ethanolamine, triethanolamine, dicyclohexylamine, N,N'-dibenzylethylenediamine, etc.), salts with basic amino acids (e.g. arginine etc.) and the like.

The quinazoline derivative (I) and pharmaceutically acceptable salt according to this invention have uricosuric activity and are, therefore, of value as the active ingredient of uricosuric compositions.

The uricosuric composition according to this invention is effective in the treatment and prevention of gout or the like. The active ingredient, quinazoline derivative (I) or pharmaceutically acceptable salt thereof, may be administered as such but is generally administered as formulated into various pharmaceutically acceptable compositions.

As dosage forms useful for such compositions, there may be mentioned injections, capsules, granules, powders, tablets and so on.

Such pharmaceutical compositions are formulated by the established pharmaceutical procedures using excipients (e.g. sucrose, starch, mannit, sorbit, lactose, glucose, cellulose, talc, calcium phosphate, calcium carbonate, etc.), binding agents (e.g. cellulose, methyl cellulose, hydroxypropylmethyl cellulose, polypropylpyrrolidone, gelatin, gum arabic, polyethylene glycol, sucrose, starch, etc.), disintegrators (e.g. starch, carboxymethyl cellulose, hydroxypropyl starch, sodium bicarbonate, calcium phosphate, calcium citrate, etc.), lubricants (e.g. magnesium stearate, talc, sodium laurylsulfate, etc.), flavoring agents (e.g. citric acid, mentol, glycine, orange powders, etc.), preservatives (e.g. sodium benzoate, sodium bisulfite, methylparaben, propylparaben, etc.), stabilizers (e.g. citric acid, sodium citrate, acetic acid, etc.), suspending agents (e.g. methyl cellulose, polyvinylpyrrolidone, aluminum stearate, etc.), dispersing agents (e.g. hydroxypropylmethyl cellulose, etc.), solvents (e.g. water, etc.), base wax (e.g. cacao butter, white petrolatum, polyethylene glycol, etc.) and so on.

While the dosage of the uricosuric composition according to this invention is dependent on the patient's age and body weight, clinical condition, method of administration, etc., a daily dose of generally 10 to 1800 mg as quinazoline derivative (I) or a pharmaceutically acceptable salt thereof, or preferably 30 to 1200 mg on the same basis, is administered orally or parenterally in a single dose to 3 divided doses.

The following test examples are intended to illustrate the excellent uricosuric action and low toxicity of the quinazoline derivative (I) or pharmaceutically acceptable salt thereof.

Test Compound (1) 2-[7-Chloro-3-(4-bromo-2-fluorobenzyl)-1,2,3,4-tetrahydro-2,4-dioxoquinazolin-1-acetic acid (hereinafter referred to briefly as compound A).

(2) 2-[7-Fluoro-3-(4-bromo-2-fluorobenzyl)-1,2,3,4-tetrahydro-2,4-dioxoquinazolin-1-yl]acetic acid (hereinafter referred to briefly as compound B).

(a) Uricosuric action:

Method

Compound A, in a single dose of 600 mg (two capsules according to the example (1) given hereinafter), was administered orally to six humans (healthy male adult volunteers) and the serum uric acid level was determined for 48 hours after administration.

The results are shown in the following table.

| Determination schedule | Serum uric acid concentration (mg/dl) Mean ± standard deviation (N = 6) |
|---|---|
| Before administration | 5.5500 ± 0.9439 |
| 4 Hrs. after administration | 4.5000 ± 0.6542* |
| 8 Hrs. after administration | 4.0333 ± 0.6250** |
| 12 Hrs. after administration | 4.1667 ± 0.7448** |
| 24 Hrs. after administration | 4.3167 ± 0.7360* |
| 48 Hrs. after administration | 4.5167 ± 0.5981* |

*, **: significant decreases from the baseline before administration (*: P < 0.05; **: P < 0.01)

(b) The effect of Compound B on uric acid excretion in female rats

Method

Female SD rats (6 weeks old) were fasted for 18 hours and submitted to the test (3 animals per group).

Compound B was suspended in 0.5% methylcellulose solution and the suspension was orally administered in a dosing volume of 5 ml/kg.

At the same time, the animals were orally loaded with 20 ml/kg of physiological saline. Urine samples were collected up to 6 hours after drug administration. The uric acid in each urine sample was assayed by HPLC.

Results

| Dose (mg/kg, p.o.) | Number of groups | Excretion of uric acid (mg/kg) |
|---|---|---|
| 0 | 3 | 3.07 ± 0.44 |
| 10 | 3 | 3.36 ± 0.14 |
| 100 | 3 | 4.02 ± 0.18 |
| 320 | 3 | 4.88 ± 0.24* |

Period for collection of urine: 0-6 hr
Mean ± S.E.
*: $P < 0.05$

(c) Acute Toxicity

Male SD rats (5 animals per group) were orally dosed with a suspension of the test compound in 0.5% methylcellulose solution and observed for 14 days after oral administration.

Results

|  | $LD_{50}$ |
|---|---|
| Compound A | 4250 mg/kg |
| Compound B | 2144 mg/kg |

EXAMPLES

Example 1

A powder of the following formula is encapsulated to provide a capsule.

Formula

Compound A:300 mg
Low-substituted hydroxypropylcellulose:30 mg
Polyoxyl 40 Stearate:3 mg
Hydroxypropylcellulose:3 mg

Example 2

The ingredients in the following formula are blended and granulated into granules in a conventional manner.

Formula for Granules

Compound A:30.0% (by weight)
Lactose:69.4%
Polyoxyl 40 Stearate:0.1%
Hydroxypropylcellulose:0.5%

Example 3

The ingredients in the following formula are blended and powdered into powders in a conventional manner.

Formula for Powders

Compound A:30.0% (by weight)
Lactose:69.4%
Polyoxyl 40 Stearate:0.1%
Hydroxypropylcellulose:0.5%

Example 4

The ingredients in the following formula are blended and compressed into tablets in a conventional manner.

Formula for a Tablet

| Formula for a tablet | |
|---|---|
| Compound A | 300 (mg) |
| Lactose | 100.8 |
| Cross-Linked sodium carboxymethylcellulose | 9 |
| Hydroxypropylcellulose | 3 |
| Polyoxyl 40 Stearate | 3 |
| Magnesium Stearate | 4.2 |
| | 420 mg/tablet |

Thus obtained tablets are, when desired, coated with film-coating or enteric coating.

Example 5

Compound A (5 g) and sodium hydroxide (450 mg) are dissolved in distilled water for injection to give injectable solution (10 l) and the injectable solution is divided to 100 ampoules in a conventional manner.
The above-mentioned compositions (capsule, granule, powder, tablet, injection) are also prepared by using compound B instead of compound A.

What we claim is:

1. A method for treating gout which comprises administering a uricosuric effective amount of a quinazoline derivative of the general formula:

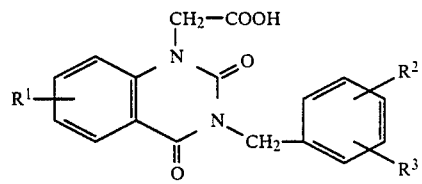

wherein $R^1$, $R^2$ and $R^3$ each is a hydrogen atom or a halogen atom or a pharmaceutically acceptable salt thereof a human being in need thereof.

2. A method for excreting uric acid which comprises administering a uricosuric effective amount of a quinazoline derivative of the general formula:

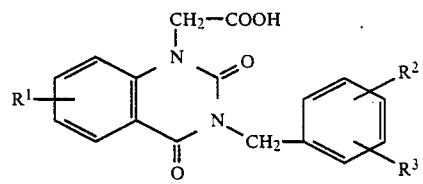

wherein $R^1$, $R^2$ and $R^3$ each is a hydrogen atom or a halogen atom or a pharmaceutically acceptable salt thereof to a human being in need thereof.

3. A method for lowering the uric acid concentration in serum which comprises administering a uricosuric effective amount of a quinazoline derivative of the general formula:

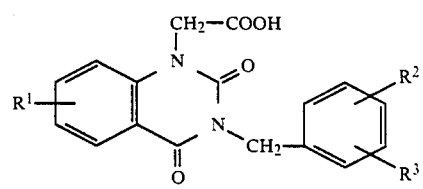

wherein $R^1$, $R^2$ and $R^3$ each is a hydrogen atom or a halogen atom or a pharmaceutically acceptable salt thereof to a human being in need thereof.

* * * * *